US012575807B2

(12) United States Patent
Minas

(10) Patent No.: US 12,575,807 B2
(45) Date of Patent: Mar. 17, 2026

(54) REINFORCEMENT LAYER FOR INTRALUMINAL IMAGING DEVICE

(71) Applicant: PHILIPS IMAGE GUIDED THERAPY CORPORATION, San Diego, CA (US)

(72) Inventor: Maritess Minas, San Diego, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 296 days.

(21) Appl. No.: 18/272,135

(22) PCT Filed: Jan. 14, 2022

(86) PCT No.: PCT/EP2022/050714
§ 371 (c)(1),
(2) Date: Jul. 13, 2023

(87) PCT Pub. No.: WO2022/152828
PCT Pub. Date: Jul. 21, 2022

(65) Prior Publication Data
US 2024/0138807 A1     May 2, 2024

Related U.S. Application Data

(60) Provisional application No. 63/137,547, filed on Jan. 14, 2021.

(51) Int. Cl.
*A61B 8/00*     (2006.01)
*A61B 8/12*     (2006.01)

(52) U.S. Cl.
CPC ............... *A61B 8/12* (2013.01); *A61B 8/445* (2013.01); *A61B 8/4488* (2013.01)

(58) Field of Classification Search
None
See application file for complete search history.

(56) References Cited

U.S. PATENT DOCUMENTS 6,776,763 B2     8/2004 Nix
7,226,417 B1     6/2007 Eberle
(Continued)

FOREIGN PATENT DOCUMENTS

EP          3590437 A1     1/2020
WO       2020144159 A1     7/2020
WO       2022018008 A1     1/2022

OTHER PUBLICATIONS

International Search Report and Written Opinion of PCT/EP2022/050714, dated Apr. 7, 2022.

*Primary Examiner* — Sana Sahand

(57) ABSTRACT

An intraluminal imaging device, includes a flexible elongate member configured to be positioned within a body lumen of a patient. The flexible elongate member includes a proximal portion and a distal portion. The imaging device further includes an ultrasound scanner assembly configured to obtain ultrasound imaging data while positioned within the body lumen. The ultrasound scanner assembly is coupled to and positioned distally of the distal portion of the flexible elongate member. The distal portion of the flexible elongate member includes a first polymer with a first hardness. The imaging device further includes a reinforcement layer extending over and directly contacting only a region of the distal portion of the flexible elongate member. The reinforcement layer includes a second polymer with a different, second hardness.

15 Claims, 11 Drawing Sheets

(56)     References Cited

U.S. PATENT DOCUMENTS 7,846,101  B2     12/2010  Eberle
2015/0305710  A1     10/2015  Stigall

700

710 — Apply reinforcement layer to distal portion of flexible elongate member

720 — Thermally reflow reinforcement layer

730 — Join distal portion of flexible elongate member to proximal portion of scanner assembly

REINFORCEMENT LAYER FOR INTRALUMINAL IMAGING DEVICE

TECHNICAL FIELD

The present disclosure relates generally to intraluminal imaging devices and, in particular, to intraluminal imaging devices comprising a reinforcement layer extending over and directly contacting a region of a distal portion of a flexible elongate member. For example, the reinforcement layer may transition a stiffness of the region so that the region is bendable to a radius of curvature without kinking.

BACKGROUND

Intravascular ultrasound (IVUS) imaging is widely used in interventional cardiology as a diagnostic tool for assessing a diseased vessel, such as an artery, within the human body to determine the need for treatment, to guide the intervention, and/or to assess its effectiveness. An IVUS device including one or more ultrasound transducers is passed into the vessel and guided to the area to be imaged. The transducers emit ultrasonic energy in order to create an image of the vessel of interest. Ultrasonic waves are partially reflected by discontinuities arising from tissue structures (such as the various layers of the vessel wall), red blood cells, and other features of interest. Echoes from the reflected waves are received by the transducer and passed along to an IVUS imaging system. The imaging system processes the received ultrasound echoes to produce a cross-sectional image of the vessel where the device is placed.

Phased array (also known as synthetic-aperture) IVUS catheters are a type of IVUS device commonly used today. Phased array IVUS catheters carry a scanner assembly that includes an array of ultrasound transducers positioned and distributed around its perimeter or circumference along with one or more integrated circuit controller chips mounted adjacent to the transducer array. The controllers select individual acoustic elements (or groups of elements) for transmitting a pulse of acoustic energy and for receiving the ultrasound echo signal corresponding to the transmitted ultrasound energy. By stepping through a sequence of transmit-receive pairs, the phased array IVUS system can synthesize the effect of a mechanically scanned ultrasound transducer but without moving parts (hence the solid-state designation). Since there is no rotating mechanical element, the transducer array can be placed in direct contact with the blood and vessel tissue with minimal risk of vessel trauma and without a need for an additional housing between the rotating element and the vessel lumen.

IVUS catheters must be stiff enough to be pushable so that a clinician can advance them through the tortuous pathways of human vasculature. However, to facilitate navigation through these tortuous pathways, the catheters must also be flexible. For instance, the catheters may require flexibility to bend around turns within the vasculature. Balancing the stiffness and flexibility of the catheters may be challenging and may be further complicated by attempts to limit kinking of the catheters during bending.

SUMMARY

Disclosed herein is an intraluminal imaging device (e.g., an intravascular ultrasound or IVUS imaging device) that may be navigated through tortuous vasculature, such as coronary vasculature. The device includes a flexible elongate member (e.g., a catheter) and an imaging assembly (e.g., a scanner assembly) for obtaining intraluminal image data. A reinforcement layer is coupled to and extends over a region within a distal portion of the flexible elongate member that is proximal to the imaging assembly. For instance, the region may be proximal of a joint between the flexible elongate member and the imaging assembly. The reinforcement layer may transition a stiffness (e.g., a flexibility) of the flexible elongate member (e.g., an outer member of the flexible elongate member) to the imaging assembly, which may be more rigid than the flexible elongate member. By coupling the reinforcement layer with the region, the column strength of the region may be increased, and the region may be more resistant to kinking when bent. To that end, the reinforcement layer may decrease the radius of curvature that the intraluminal imaging device may bend to without kinking so that the imaging device may navigate tighter turns without kinking. Moreover, with increased the column strength of the region, the intraluminal imaging device may maintain sufficient strength to be pushed for advancement through the vasculature.

In an exemplary aspect, an intraluminal imaging device, includes a flexible elongate member configured to be positioned within a body lumen of a patient. The flexible elongate member can include a proximal portion and a distal portion. The intraluminal imaging device can further include an ultrasound scanner assembly configured to obtain ultrasound imaging data while positioned within the body lumen. The ultrasound scanner assembly can be coupled to and positioned distally of the distal portion of the flexible elongate member. The distal portion of the flexible elongate member can include a first polymer with a first hardness. The intraluminal imaging device can further include a reinforcement layer extending over and directly contacting only a region of the distal portion of the flexible elongate member. The reinforcement layer can include a second polymer with a different, second hardness.

In some aspects, the region and the reinforcement layer can be coupled via thermal reflow. In some aspects, the region can be spaced proximally from a distal end of the distal portion of the flexible elongate member. In some aspects, the region can be spaced at least 1 millimeter from the distal end of the distal portion of the flexible elongate member.

In some aspects, the second hardness can be less than the first hardness. In some aspects, the reinforcement layer can include a thermoplastic elastomer. In some aspects, the reinforcement layer can include a thickness greater than or equal to 0.001 inches.

In some aspects, the ultrasound scanner assembly can include a conductor interface. A proximal portion of the reinforcement layer can extend over the conductor interface. In some aspects, the intraluminal imaging device can include a plurality of conductors coupled to a proximal portion of the conductor interface. The reinforcement layer can extend over the plurality of conductors.

In some aspects, a distal end of the flexible elongate member comprises a flared opening. In some aspects, the region is spaced proximally from the flared opening. In some aspects, the intraluminal imaging device is a rapid-exchange catheter comprising a guidewire entry port. The guidewire entry port can be disposed within the distal portion of the flexible elongate member. The region can be positioned distal of the guidewire entry port.

In some aspects, the intraluminal imaging device includes an additional reinforcement layer extending over and directly contacting only an additional region of the distal portion of the flexible elongate member. The additional reinforcement layer can include a third hardness different than the first hardness.

In some aspects, the flexible elongate member can be configured to bend to a radius of curvature within tortuous vasculature. The reinforcement layer can be configured to decrease the radius of curvature to which the region of the flexible elongate member is bendable within the tortuous vasculature without kinking.

In an exemplary aspect, an intravascular ultrasound (IVUS) imaging catheter, includes a catheter body configured to be positioned within a blood vessel of a patient. The catheter body can include a proximal portion and a distal portion. The IVUS imaging catheter can further include an ultrasound scanner assembly. The ultrasound scanner assembly can include a circumferential array of acoustic elements configured to obtain ultrasound imaging data while positioned within the blood vessel. The ultrasound scanner assembly can be coupled to and positioned distally of the distal portion of the catheter body. The distal portion of the catheter body can include a first polymer with a first hardness. The IVUS imaging catheter can include a reinforcement layer extending over and directly contacting only a region of the distal portion of the catheter body. The reinforcement layer can include a second polymer with a different, second hardness less than the first hardness such that the region is bendable within a tortuous portion of the blood vessel without kinking.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1A:
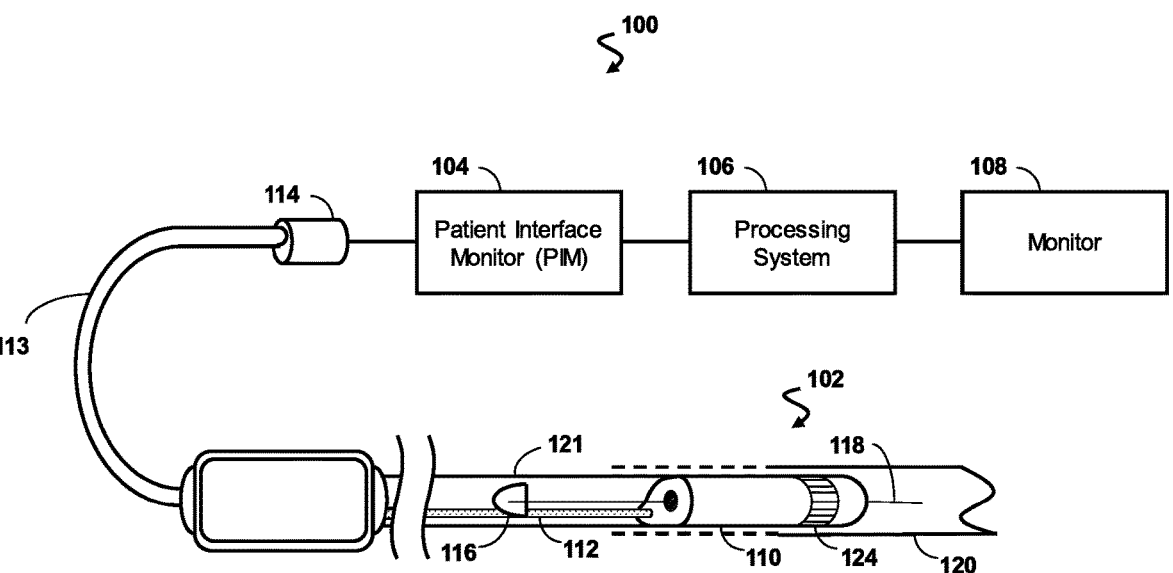
FIG. 1A is a diagrammatic schematic view of an intraluminal imaging system, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1A is a diagrammatic schematic view of an ultrasound imaging system 100, according to aspects of the present disclosure. The ultrasound imaging system 100 can be an intraluminal imaging system. In some instances, the system 100 can be an intravascular ultrasound (IVUS) imaging system. The system 100 may include an intraluminal imaging device 102 such as a catheter, guide wire, or guide catheter, a patient interface module (PIM) 104, a processing system or console 106, and a monitor 108. The intraluminal imaging device 102 can be an ultrasound imaging device. In some instances, the device 102 can be IVUS imaging device, such as a solid-state IVUS device.

At a high level, the IVUS device 102 emits ultrasonic energy, or ultrasound signals, from a transducer array 124 included in scanner assembly 110 mounted near a distal end of the catheter device. The ultrasonic energy is reflected by tissue structures in the medium, such as a vessel 120, or another body lumen surrounding the scanner assembly 110, and the ultrasound echo signals are received by the transducer array 124. In that regard, the device 102 can be sized, shaped, or otherwise configured to be positioned within the body lumen of a patient. The PIM 104 transfers the received echo signals to the console or computer 106 where the ultrasound image (possibly including flow information) is reconstructed and displayed on the monitor 108. The processing system 106 can include a processor and a memory. The processing system 106 can be operable to facilitate the features of the IVUS imaging system 100 described herein. For example, the processing system 106 can execute computer readable instructions stored on the non-transitory tangible computer readable medium.

The PIM 104 facilitates communication of signals between the processing system 106 and the scanner assembly 110 included in the IVUS device 102. This communication includes the steps of: (1) providing commands to integrated circuit controller chip(s) 206A, 206B, illustrated in FIG. 2, included in the scanner assembly 110 to select the particular transducer array element(s), or acoustic element(s), to be used for transmit and receive, (2) providing the transmit trigger signals to the integrated circuit controller chip(s) 206A, 206B included in the scanner assembly 110 to activate the transmitter circuitry to generate an electrical pulse to excite the selected transducer array element(s) 212, and/or (3) accepting amplified echo signals received from the selected transducer array element(s) 212 via amplifiers included on the integrated circuit controller chip(s) 206 of the scanner assembly 110. In some embodiments, the PIM 104 performs preliminary processing of the echo data prior to relaying the data to the console 106. In examples of such embodiments, the PIM 104 performs amplification, filtering, and/or aggregating of the data. In an embodiment, the PIM 104 also supplies high- and low-voltage DC power to support operation of the device 102 including circuitry within the scanner assembly 110.

The processing system 106 receives the echo data from the scanner assembly 110 by way of the PIM 104 and processes the data to reconstruct an image of the tissue structures in the medium surrounding the scanner assembly 110. The console 106 outputs image data such that an image of the vessel 120, such as a cross-sectional image of the vessel 120, is displayed on the monitor 108. Vessel 120 may represent fluid filled or surrounded structures, both natural and man-made. The vessel 120 may be within a body of a patient. The vessel 120 may be a blood vessel, as an artery or a vein of a patient's vascular system, including cardiac vasculature, peripheral vasculature, neural vasculature, renal vasculature, and/or or any other suitable lumen inside the body. For example, the device 102 may be used to examine any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the blood, chambers or other parts of the heart, and/or other systems of the body. In addition to natural structures, the device 102 may be used to examine man-made structures such as, but without limitation, heart valves, stents, shunts, filters and other devices.

Figure 2:
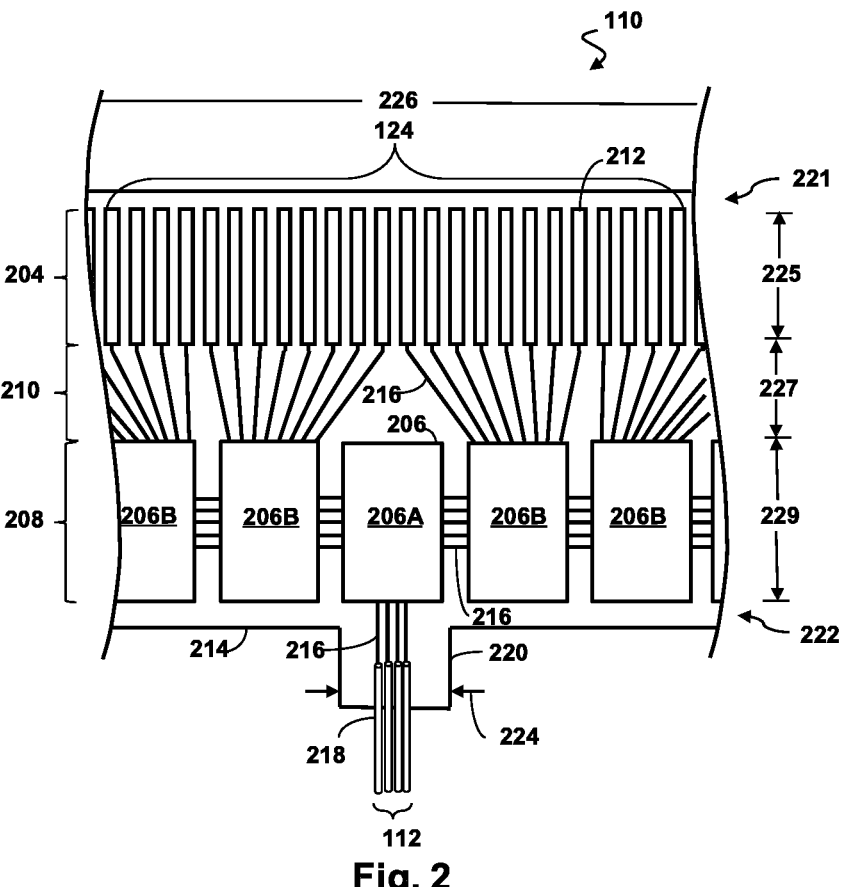
FIG. 2 is a diagrammatic view of the top of a scanner assembly in a flat configuration, according to aspects of the present disclosure.

In some embodiments, the IVUS device includes some features similar to traditional solid-state IVUS catheters, such as the EagleEye® catheter available from Koninklijke Philips N.V. and those disclosed in U.S. Pat. No. 7,846,101 hereby incorporated by reference in its entirety. For example, the IVUS device 102 includes the scanner assembly 110 near a distal end of the device 102 and a transmission line bundle 112 extending along the longitudinal body of the device 102. The transmission line bundle or cable 112 can include a plurality of conductors, including one, two, three, four, five, six, seven, or more conductors 218 (FIG. 2). Further, in some embodiments, the IVUS device 102 includes a plurality of transmission line bundles each comprising a plurality of conductors of varying size (e.g., gauge), insulation, and/or other structural and electrical characteristics. It is understood that any suitable gauge wire can be used for the conductors 218. In an embodiment, the cable 112 can include a four-conductor transmission line arrangement with, e.g., 41 AWG gauge wires. In an embodiment, the cable 112 can include a seven-conductor transmission line arrangement utilizing, e.g., 44 AWG gauge wires. In some embodiments, 43 AWG gauge wires can be used.

The transmission line bundle 112 passes through or connects to a cable 113 that terminates in a PIM connector 114 at a proximal end of the device 102. The PIM connector 114 electrically couples the transmission line bundle 112 to the PIM 104 and physically couples the IVUS device 102 to the PIM 104. In an embodiment, the IVUS device 102 further includes a guide wire exit port 116. Accordingly, in some instances the IVUS device is a rapid-exchange catheter. The guide wire exit port 116 allows a guide wire 118 to be inserted towards the distal end in order to direct the device 102 through the vessel 120.

In an embodiment, the processing system 106 generates flow data by processing the echo signals from the IVUS device 102 into Doppler power or velocity information. The processing system 106 may also generate B-mode data by applying envelope detection and logarithmic compression on the conditioned echo signals. The processing system 106 can further generate images in various views, such as 2D and/or 3D views, based on the flow data or the B-mode data. The processing system 106 can also perform various analyses and/or assessments. For example, the processing system 106 can apply virtual histology (VH) techniques, for example, to analyze or assess plaques within a vessel (e.g., the vessel 120). The images can be generated to display a reconstructed color-coded tissue map of plaque composition superimposed on a cross-sectional view of the vessel.

In an embodiment, the processing system 106 can apply a blood flow detection algorithm to determine the movement of blood flow, for example, by acquiring image data of a target region (e.g., the vessel 120) repeatedly and determining the movement of the blood flow from the image data. The blood flow detection algorithm operates based on the principle that signals measured from vascular tissue are relatively static from acquisition to acquisition, whereas signals measured from blood flow vary at a characteristic rate corresponding to the flow rate. As such, the blood flow detection algorithm may determine movements of blood flow based on variations in signals measured from the target region between repeated acquisitions. To acquire the image data repeatedly, the processing system 106 may control to the device 102 to transmit repeated pulses on the same aperture.

While the present disclosure describes embodiments related to intravascular ultrasound (IVUS) imaging using an intravascular catheter or guidewire, it is understood that one or more aspects of the present disclosure can be implemented in any suitable ultrasound imaging system, including a synthetic aperture ultrasound imaging system, a phased array ultrasound imaging system, or any other array-based ultrasound imaging system. For example, aspects of the present disclosure can be implemented in intraluminal ultrasound imaging systems using an intracardiac (ICE) echocardiography catheter and/or a transesophageal echocardiography (TEE) probe, and/or external ultrasound imaging system using an ultrasound probe configured for imaging while positioned adjacent to and/or in contact with the patient's skin. The ultrasound imaging device can be a transthoracic echocardiography (TTE) imaging device in some embodiments.

An ultrasound transducer array of the ultrasound imaging device includes an array of acoustic elements configured to emit ultrasound energy and receive echoes corresponding to the emitted ultrasound energy. In some instances, the array may include any number of ultrasound transducer elements. For example, the array can include between 2 acoustic elements and 10000 acoustic elements, including values such as 2 acoustic elements, 4 acoustic elements, acoustic elements, 64 acoustic elements, 128 acoustic elements, 500 acoustic elements, 812 acoustic elements, 3000 acoustic elements, 9000 acoustic elements, and/or other values both larger and smaller. In some instances, the transducer elements of the array may be arranged in any suitable configuration, such as a linear array, a planar array, a curved array, a curvilinear array, a circumferential array, an annular array, a phased array, a matrix array, a one-dimensional (1D) array, a 1.x dimensional array (e.g., a 1.5D array), or a two-dimensional (2D) array. The array of transducer elements (e.g., one or more rows, one or more columns, and/or one or more orientations) can be uniformly or independently controlled and activated. The array can be configured to obtain one-dimensional, two-dimensional, and/or three-dimensional images of patient anatomy.

The ultrasound transducer elements may include piezoelectric/piezoresistive elements, piezoelectric micromachined ultrasound transducer (PMUT) elements, capacitive micromachined ultrasound transducer (CMUT) elements, and/or any other suitable type of ultrasound transducer elements. The ultrasound transducer elements of the array are in communication with (e.g., electrically coupled to) electronic circuitry. For example, the electronic circuitry can include one or more transducer control logic dies. The electronic circuitry can include one or more integrated circuits (IC), such as application specific integrated circuits (ASICs). In some embodiments, one or more of the ICs can include a microbeamformer (μBF). In other embodiments, one or more of the ICs includes a multiplexer circuit (MUX).

Figure 1B:
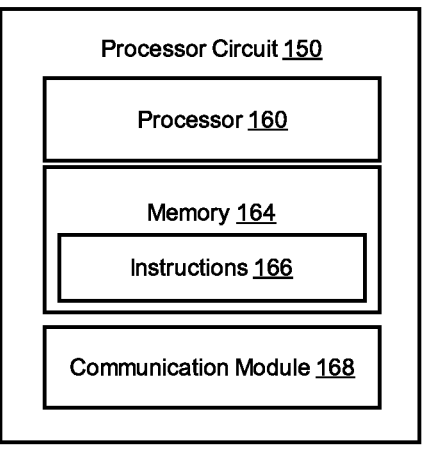
FIG. 1B is a schematic diagram of a processor circuit, according to embodiments of the present disclosure.

FIG. 1B is a schematic diagram of a processor circuit 150, according to embodiments of the present disclosure. The processor circuit 150 may be implemented in the processing system 106 and/or the imaging device 102 of FIG. 1A. As shown, the processor circuit 150 may include a processor 160, a memory 164, and a communication module 168. These elements may be in direct or indirect communication with each other, for example via one or more buses.

The processor 160 may include a central processing unit (CPU), a digital signal processor (DSP), an ASIC, a controller, an FPGA, another hardware device, a firmware device, or any combination thereof configured to perform the operations described herein. The processor 160 may also be implemented as a combination of computing devices, e.g., a combination of a DSP and a microprocessor, a plurality of microprocessors, one or more microprocessors in conjunction with a DSP core, or any other such configuration.

The memory 164 may include a cache memory (e.g., a cache memory of the processor 160), random access memory (RAM), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, other forms of volatile and non-volatile memory, or a combination of different types of memory. In an embodiment, the memory 164 includes a non-transitory computer-readable medium. The memory 164 may store instructions 166. The instructions 166 may include instructions that, when executed by the processor 160, cause the processor 160 to perform the operations described herein with reference to the processing system 106 and/or the imaging device 102 (FIG. 1A). Instructions 166 may also be referred to as code. The terms "instructions" and "code" should be interpreted broadly to include any type of computer-readable statement(s). For example, the terms "instructions" and "code" may refer to one or more programs, routines, sub-routines, functions, procedures, etc. "Instructions" and "code" may include a single computer-readable statement or many computer-readable statements.

The communication module 168 can include any electronic circuitry and/or logic circuitry to facilitate direct or indirect communication of data between the processor circuit 150, the imaging device 102, and/or the display 108. In that regard, the communication module 168 can be an input/output (I/O) device. In some instances, the communication module 168 facilitates direct or indirect communication between various elements of the processor circuit 150 and/or the processing system 106 (FIG. 1A).

FIG. 2 is a diagrammatic top view of a portion of a flexible assembly 200, according to aspects of the present disclosure. The flexible assembly 200 includes a transducer array 124 formed in a transducer region 204 and transducer control logic dies 206 (including dies 206A and 206B) formed in a control region 208, with a transition region 210 disposed therebetween.

The transducer control logic dies 206 are mounted on a flexible substrate 214 into which the transducers 212 have been previously integrated. The flexible substrate 214 is shown in a flat configuration in FIG. 2. Though six control logic dies 206 are shown in FIG. 2, any number of control logic dies 206 may be used. For example, one, two, three, four, five, six, seven, eight, nine, ten, or more control logic dies 206 may be used.

The flexible substrate 214, on which the transducer control logic dies 206 and the transducers 212 are mounted, provides structural support and interconnects for electrical coupling. The flexible substrate 214 may be constructed to include a film layer of a flexible polyimide material such as KAPTON™ (trademark of DuPont). Other suitable materials include polyester films, polyimide films, polyethylene napthalate films, or polyetherimide films, liquid crystal polymer, other flexible printed semiconductor substrates as well as products such as Upilex® (registered trademark of Ube Industries) and TEFLON® (registered trademark of E.I. du Pont). In the flat configuration illustrated in FIG. 2, the flexible substrate 214 has a generally rectangular shape. As shown and described herein, the flexible substrate 214 is configured to be wrapped around a support member 230 (FIG. 3) in some instances. Therefore, the thickness of the film layer of the flexible substrate 214 is generally related to the degree of curvature in the final assembled flexible assembly 200. In some embodiments, the film layer is between 5 μm and 100 μm, with some particular embodiments being between 5 μm and 25.1 μm, e.g., 6 μm.

The transducer control logic dies 206 is a non-limiting example of a control circuit. The transducer region 204 is disposed at a distal portion 221 of the flexible substrate 214. The control region 208 is disposed at a proximal portion 222 of the flexible substrate 214. The transition region 210 is disposed between the control region 208 and the transducer region 204. Dimensions of the transducer region 204, the control region 208, and the transition region 210 (e.g., lengths 225, 227, 229) can vary in different embodiments. In some embodiments, the lengths 225, 227, 229 can be substantially similar or, the length 227 of the transition region 210 may be less than lengths 225 and 229, the length 227 of the transition region 210 can be greater than lengths 225, 229 of the transducer region and controller region, respectively.

The control logic dies 206 are not necessarily homogenous. In some embodiments, a single controller is designated a master control logic die 206A and contains the communication interface for the transmission line bundle 112, which may serve as an electrical communication bus between a processing system, e.g., processing system 106, and the flexible assembly 200. Accordingly, the master control circuit may include control logic that decodes control signals received over the transmission line bundle 112, transmits control responses over the transmission line bundle 112, amplifies echo signals, and/or transmits the echo signals over the transmission line bundle 112. The remaining controllers are slave controllers 206B. The slave controllers 206B may include control logic that drives a transducer 212 to emit an ultrasonic signal and selects a transducer 212 to receive an echo. In the depicted embodiment, the master controller 206A does not directly control any transducers 212. In other embodiments, the master controller 206A drives the same number of transducers 212 as the slave controllers 206B or drives a reduced set of transducers 212 as compared to the slave controllers 206B. In an exemplary embodiment, a single master controller 206A and eight slave controllers 206B are provided with eight transducers assigned to each slave controller 206B.

To electrically interconnect the control logic dies 206 and the transducers 212, in an embodiment, the flexible substrate 214 includes conductive traces 216 formed in the film layer that carry signals between the control logic dies 206 and the transducers 212. In particular, the conductive traces 216 providing communication between the control logic dies 206 and the transducers 212 extend along the flexible substrate 214 within the transition region 210. In some instances, the conductive traces 216 can also facilitate electrical communication between the master controller 206A and the slave controllers 206B. The conductive traces 216 can also provide a set of conductive pads that contact the conductors 218 of the transmission line bundle 112 when the conductors 218 of the transmission line bundle 112 are mechanically and electrically coupled to the flexible substrate 214. Suitable materials for the conductive traces 216 include copper, gold, aluminum, silver, tantalum, nickel, and tin, and may be deposited on the flexible substrate 214 by processes such as sputtering, plating, and etching. In an embodiment, the flexible substrate 214 includes a chromium adhesion layer. The width and thickness of the conductive traces 216 are selected to provide proper conductivity and resilience when the flexible substrate 214 is rolled. In that regard, an exemplary range for the thickness of a conductive trace 216 and/or conductive pad is between 1-5 μm. For example, in an embodiment, 5 μm conductive traces 216 are separated by 5 μm of space. The width of a conductive trace 216 on the flexible substrate may be further determined by the width of the conductor 218 to be coupled to the trace/pad.

The flexible substrate 214 can include a conductor interface 220 (e.g., a weld leg) in some embodiments. The conductor interface 220 can be a location of the flexible substrate 214 where the conductors 218 of the transmission line bundle 112 are coupled to the flexible substrate 214. For example, the bare conductors of the transmission line bundle 112 are electrically coupled to the flexible substrate 214 at the conductor interface 220. The conductor interface 220 can be a tab extending from the main body of flexible substrate 214. In that regard, the main body of the flexible substrate 214 can refer collectively to the transducer region 204, controller region 208, and the transition region 210. In the illustrated embodiment, the conductor interface 220 extends from the proximal portion 222 of the flexible substrate 214. In other embodiments, the conductor interface 220 is positioned at other parts of the flexible substrate 214, such as the distal portion 221, or the flexible substrate 214 may lack the conductor interface 220. A value of a dimension of the tab or conductor interface 220, such as a width 224, can be less than the value of a dimension of the main body of the flexible substrate 214, such as a width 226. In some embodiments, the substrate forming the conductor interface 220 is made of the same material(s) and/or is similarly flexible as the flexible substrate 214. In other embodiments, the conductor interface 220 is made of different materials and/or is comparatively more rigid than the flexible substrate 214. For example, the conductor interface 220 can be made of a plastic, thermoplastic, polymer, hard polymer, etc., including polyoxymethylene (e.g., DELRIN®), polyether ether ketone (PEEK), nylon, Liquid Crystal Polymer (LCP), and/or other suitable materials.

Figure 3:
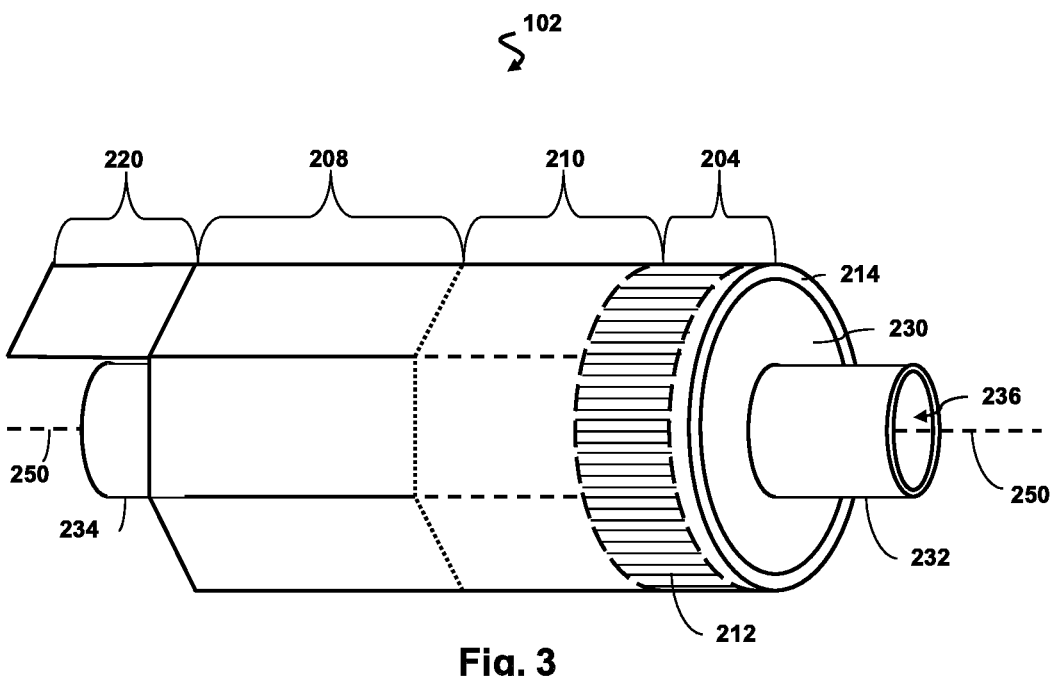
FIG. 3 is a diagrammatic perspective view of the scanner assembly shown in FIG. 2 in a rolled configuration around a support member, according to aspects of the present disclosure.

FIG. 3 illustrates a perspective view of the device 102 with the scanner assembly 200 in a rolled configuration. In some instances, the assembly 200 is transitioned from a flat configuration (FIG. 2) to a rolled or more cylindrical configuration (FIG. 3). For example, in some embodiments, techniques are utilized as disclosed in one or more of U.S. Pat. No. 6,776,763, titled "ULTRASONIC TRANSDUCER ARRAY AND METHOD OF MANUFACTURING THE SAME" and U.S. Pat. No. 7,226,417, titled "HIGH RESOLUTION INTRAVASCULAR ULTRASOUND SENSING ASSEMBLY HAVING A FLEXIBLE SUBSTRATE," each of which is hereby incorporated by reference in its entirety.

In some embodiments, the transducer elements 212 and/or the controllers 206 can be positioned in in an annular configuration, such as a circular configuration or in a polygon configuration, around a longitudinal axis 250 of a support member 230. It will be understood that the longitudinal axis 250 of the support member 230 may also be referred to as the longitudinal axis of the scanner assembly 200, the flexible elongate member 121, and/or the device 102. For example, a cross-sectional profile of the imaging assembly 200 at the transducer elements 212 and/or the controllers 206 can be a circle or a polygon. Any suitable annular polygon shape can be implemented, such as a based on the number of controllers/transducers, flexibility of the controllers/transducers, etc., including a pentagon, hexagon, heptagon, octagon, nonagon, decagon, etc. In some examples, the plurality of transducer controllers 206 may be used for controlling the plurality of ultrasound transducer elements 212 to obtain imaging data associated with the vessel 120.

The support member 230 can be referenced as a unibody in some instances. The support member 230 can be composed of a metallic material, such as stainless steel, or non-metallic material, such as a plastic or polymer as described in U.S. Provisional Application No. 61/985,220, "Pre-Doped Solid Substrate for Intravascular Devices," filed Apr. 28, 2014, ('220 application) the entirety of which is hereby incorporated by reference herein. The support member 230 can be a ferrule having a distal flange or portion 232 and a proximal flange or portion 234. The support member 230 can be tubular in shape and define a lumen 236 extending longitudinally therethrough. The lumen 236 can be sized and shaped to receive the guide wire 118. The support member 230 can be manufactured using any suitable process. For example, the support member 230 can be machined and/or electrochemically machined or laser milled, such as by removing material from a blank to shape the support member 230, or molded, such as by an injection molding process.

Figure 4:
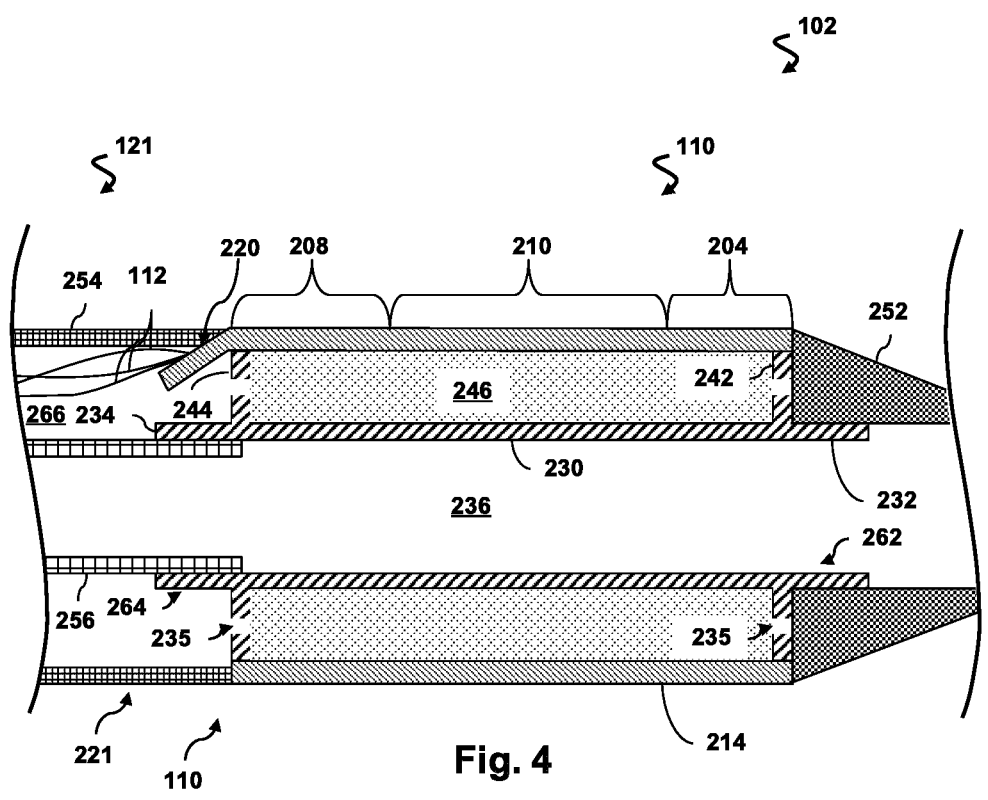
FIG. 4 is a diagrammatic cross-sectional side view of a scanner assembly in a rolled configuration around a support member, according to aspects of the present disclosure.

FIG. 4 is a diagrammatic cross-sectional side view of a distal portion of the intraluminal imaging device 102, including the flexible substrate 214 and the support member 230, according to aspects of the present disclosure. The support member 230 can be referenced as a unibody in some instances. The support member 230 can be composed of a metallic material, such as stainless steel, or non-metallic material, such as a plastic or polymer as described in U.S. Provisional Application No. 61/985,220, "Pre-Doped Solid Substrate for Intravascular Devices," filed Apr. 28, 2014, the entirety of which is hereby incorporated by reference herein. The support member 230 can be a ferrule having a distal portion 262 and a proximal portion 264. The support member 230 can define a lumen 236 extending along the longitudinal axis LA. The lumen 236 is in communication with the entry/exit port 116 and is sized and shaped to receive the guide wire 118 (FIG. 1A). The support member 230 can be manufactured according to any suitable process. For example, the support member 230 can be machined and/or electrochemically machined or laser milled, such as by removing material from a blank to shape the support member 230, or molded, such as by an injection molding process. In some embodiments, the support member 230 may be integrally formed as a unitary structure, while in other embodiments the support member 230 may be formed of different components, such as a ferrule and stands 242, 244, that are fixedly coupled to one another. In some cases, the support member 230 and/or one or more components thereof may be completely integrated with inner member 256. In some cases, the inner member 256 and the support member 230 may be joined as one, e.g., in the case of a polymer support member.

Stands 242, 244 that extend vertically are provided at the distal and proximal portions 262, 264, respectively, of the support member 230. The stands 242, 244 elevate and support the distal and proximal portions of the flexible substrate 214. In that regard, portions of the flexible substrate 214, such as the transducer portion or region 204, can be spaced from a central body portion of the support member 230 extending between the stands 242, 244. The stands 242, 244 can have the same outer diameter or different outer diameters. For example, the distal stand 242 can have a larger or smaller outer diameter than the proximal stand 244 and can also have special features for rotational alignment as well as control chip placement and connection. To improve acoustic performance, any cavities between the flexible substrate 214 and the surface of the support member 230 are filled with a backing material 246. The liquid backing material 246 can be introduced between the flexible substrate 214 and the support member 230 via passageways 235 in the stands 242, 244. In some embodiments, suction can be applied via the passageways 235 of one of the stands 242, 244, while the liquid backing material 246 is fed between the flexible substrate 214 and the support member 230 via the passageways 235 of the other of the stands 242, 244. The backing material can be cured to allow it to solidify and set. In various embodiments, the support member 230 includes more than two stands 242, 244, only one of the stands 242, 244, or neither of the stands. In that regard the support member 230 can have an increased diameter distal portion 262 and/or increased diameter proximal portion 264 that is sized and shaped to elevate and support the distal and/or proximal portions of the flexible substrate 214.

The support member 230 can be substantially cylindrical in some embodiments. Other shapes of the support member 230 are also contemplated including geometrical, non-geometrical, symmetrical, non-symmetrical, cross-sectional profiles. As the term is used herein, the shape of the support member 230 may reference a cross-sectional profile of the support member 230. Different portions the support member 230 can be variously shaped in other embodiments. For example, the proximal portion 264 can have a larger outer diameter than the outer diameters of the distal portion 262 or a central portion extending between the distal and proximal portions 262, 264. In some embodiments, an inner diameter of the support member 230 (e.g., the diameter of the lumen 236) can correspondingly increase or decrease as the outer diameter changes. In other embodiments, the inner diameter of the support member 230 remains the same despite variations in the outer diameter.

An inner member 256 and an outer member 254 (e.g., an outer shaft) are coupled to the proximal portion 264 of the support member 230. The inner member 256 and/or the outer member 254 can be included in a flexible elongate member, such as flexible elongate member 121. For instance, the inner member 256 and/or the outer member 254 shown may illustrate a distal end of the flexible elongate member 121. To that end, the coupling between the inner member 256 and/or the outer member 254 with the support member 230 may illustrate a join between the flexible elongate member 121 and the scanner assembly 110. The inner member 256 can be received within a proximal flange 234. The outer member 254 abuts and is in contact with the flexible substrate 214. A distal member 252 is coupled to the distal portion 262 of the support member 230. For example, the distal member 252 is positioned around the distal flange 232. The distal member 252 can abut and be in contact with the flexible substrate 214 and the stand 242. The distal member 252 can be the distal-most component of the intraluminal imaging device 102.

One or more adhesives can be disposed between various components at the distal portion of the intraluminal imaging device 102. For example, one or more of the flexible substrate 214, the support member 230, the distal member 252, the inner member 256, and/or the outer member 254 can be coupled to one another via an adhesive.

The conductor interface 220 is positioned at a proximal end of the substrate 214 and provides a point of electrical contact for the transmission line bundle 112. As described above, the transmission line bundle 112 may comprise a plurality of conductors configured to carry signals to and from the electrical components positioned on the substrate. The conductors of the transmission line bundle 112 are sized, shaped, and otherwise configured to be positioned within the space 266 between the outer member 254 and the inner member 256.

As described above, space available within the spaces provided in the elongate body of the catheter (e.g., within the outer member 254) may be limited. One approach to positioning the conductors of the transmission line bundle 112 within the limited spaces of the catheter is to use a single group of small-gauge wires or ribbons spanning an entire length of the catheter from the scanner assembly to the PIM. The conductors of the bundle 112 may be bundled together to form one or more twisted pairs, twisted quads, twisted groups, or other arrangements of conductors. In some embodiments, one or more of the conductors is non-twisted, such that it runs parallel with one or more conductors or twisted groups of conductors.

It will be understood that, while the embodiments described below include IVUS imaging catheters, the present disclosure contemplates that the described structural features and/or arrangements may be used in other types of intraluminal devices, including sensing catheters, guide catheters, imaging probes, sensing probes, or any other suitable type of device.

As described herein, the intraluminal imaging device 102 may include a scanner assembly 110, which may be coupled to the outer member 254 (e.g., a flexible elongate member), such as a catheter body. Moreover, in some embodiments, the scanner assembly 110 may be relatively more rigid than the outer member 254. For instance, the flexible substrate 214, the electrical and/or acoustic components coupled to the flexible substrate 214 (e.g., the integrated circuit controller chip(s) 206, the transducer array 124, and/or the like), and/or the support member 230 may bend less readily than the outer member 254. As such, as the intraluminal imaging device 102 is navigated (e.g., manipulated) through a patient's vasculature, the scanner assembly 110 may more readily maintain its shape, while the outer member 254 may bend or deform, as illustrated in FIGS. 5A-C.

Figure 5A:
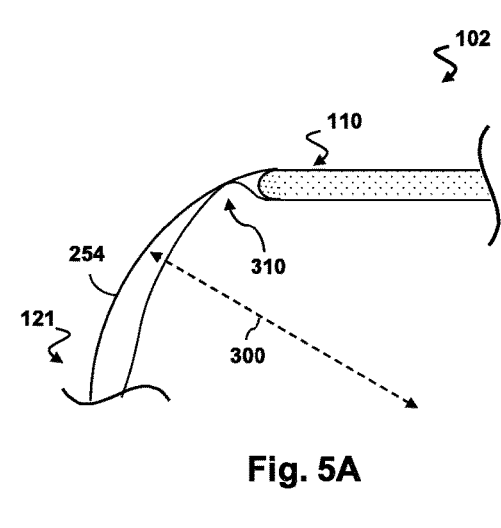
FIG. 5A is a diagrammatic side view of an intraluminal imaging device bent along a radius of curvature, in accordance with at least one embodiment of the present disclosure.
Figure 5B:
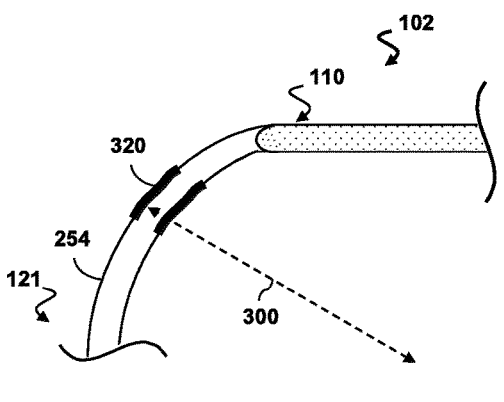
FIG. 5B is a diagrammatic side view of an intraluminal imaging device bent along a radius of curvature, in accordance with at least one embodiment of the present disclosure.
Figure 5C:
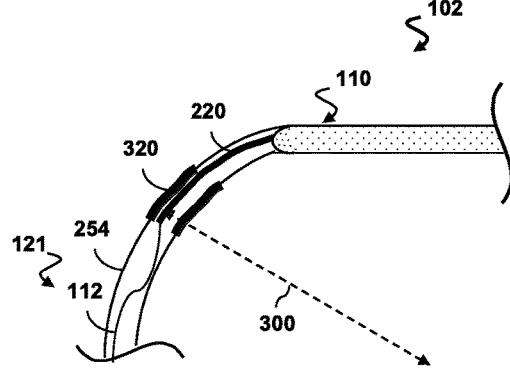
FIG. 5C is a diagrammatic side view of an intraluminal imaging device bent along a radius of curvature, in accordance with at least one embodiment of the present disclosure.

Turning now to FIGS. 5A-C, diagrammatic schematic views of examples of the intraluminal imaging device 102 bending along a radius of curvature 300 are illustrated. For the purposes of example, FIGS. 5A and 5B illustrate simplified examples of the intraluminal imaging device 102, which include the scanner assembly 110 and the outer member 254. The exemplary intraluminal imaging device 102 illustrated in FIG. 5C includes the scanner assembly 110 and the outer member 254, as well as the transmission line bundle 112 and the conductor interface 220. Further, the radius of curvature 300 may correspond to a turn (e.g., bend or other tortuosity) in a patient's vasculature. More specifically, the radius of curvature 300 may correspond to the radius of curvature that the intraluminal imaging device 102 may be bent to for navigation of through tortuous vasculature, such as cardiac vasculature.

As illustrated in FIG. 5A, bending the intraluminal imaging device 102 along the radius of curvature 300 may cause a kink 310 in the outer member 254, which may be relatively less rigid than the scanner assembly 110. In some cases, the kink 310 may prevent the intraluminal imaging device 102 from being advanced through a patient's vasculature. Additionally or alternatively, the kink 310 may result in imaging, electronic, and/or mechanical failures at the intraluminal imaging device 102. For instance, the outer member 254 may apply pressure to one or more of the conductors of the transmission line bundle 112 via the kink 310, which may damage or break the one or more conductors. As a result, power, data, and/or control signals may be prevented from being communicated with the scanner assembly 110, which may disrupt operations, such as intraluminal imaging, performed at the scanner assembly 110.

Accordingly, in some embodiments, the outer member 254 may be reinforced with a reinforcement layer 320 (e.g., a wall or coating), as illustrated in FIGS. 5B and 5C. In some embodiments, for example, the reinforcement layer 320 may be a polymer, such as a thermoplastic elastomer (e.g., PEBAX®, registered trademark of ARKEMA), which may be coupled to the outer member 254 via thermal reflow. That is, for example, the reinforcement layer 320 and the outer member 254 may be heated (e.g., melted) so that the material of the reinforcement layer 320 is fused (e.g., combined) with the material of the outer member 254.

The reinforcement layer 320 advantageously provides a transition in the stiffness (e.g., a flexibility) from the outer member 254 to the scanner assembly 110. For instance, a region of the outer member 254 lacking the reinforcement layer 320 may have a first hardness, a region of the outer member 254 coupled with the reinforcement layer 320 via thermal reflow may have a second hardness greater than the first hardness, and the scanner assembly 110 may have a third hardness greater than the second hardness. Material with a relatively greater hardness may have a relatively lesser flexibility (e.g., greater stiffness) and vice versa. In some embodiments, the region of the outer member 254 with the first hardness may be proximal of the region of the outer member 254 with the second hardness (e.g., the region reinforced by the reinforcement layer) and the scanner assembly 110, and the region of the outer member 254 with the second hardness may be between the region of the outer member 254 with the first hardness and the scanner assembly 110 such that the outer member 254 includes a change in stiffness proximal of the scanner assembly 110.

Further, in some embodiments, the reinforcement layer 320 may transition the stiffness of the outer member 254 by having a hardness (e.g., a durometer) that is relatively lower than the hardness of the outer member 254. In particular, the reinforcement layer 320 may be selected to produce a region of the outer member 254 with a hardness less than the scanner assembly 110 and greater than a hardness of another region of the outer member lacking the reinforcement layer 320. To that end, the reinforcement layer 320 may be selected (e.g., with a hardness less than hardness of the outer member 254) to advantageously provide a change (e.g., a gradual decrease) in stiffness of the intraluminal imaging device 102 proximal of the scanner assembly 110. The reinforcement layer 320 does not extend the stiff length of the scanner assembly 110 even though the reinforcement layer 320 is additional material around the outer member 254 because of the respective material properties (e.g., hardness/flexibility) of the reinforcement layer 320, the outer member 254, and the scanner assembly 110. In an illustrative example, a durometer of the outer member 254 may be 70 Shore D, while a durometer of the reinforcement layer 320 may be 55 Shore D.

By coupling the reinforcement layer 320 with a region of the outer member 254 via thermal reflow, the column strength and hardness of the region of the outer member 254 may be increased, and the outer member 254 may be more resistant to kinking when bent. For instance, for the same radius of curvature 300 as illustrated in FIG. 5A, the intraluminal imaging device 102 illustrated in FIG. 5B may bend without kinking. In other words, the kink 310 may be absent from the outer member 254 reinforced with a reinforcement layer 320, as illustrated. To that end, the reinforcement layer 320 may decrease the radius of curvature that the intraluminal imaging device 102 may bend to without kinking so that the imaging device 102 may navigate tighter turns without kinking. Moreover, with increased the column strength of the region of the outer member 254, the intraluminal imaging device 102 may maintain sufficient strength to be pushable through the vasculature.

FIG. 5C illustrates that by applying the reinforcement layer 320 to the outer member 254, the conductor interface 220, as well as the transmission line bundle 112, may remain undamaged when the intraluminal imaging device 102 is bent along the radius of curvature 300. That is, for example, because the outer member 254 lacks a kink, the outer member 254 may not apply pressure to (e.g., pinch) the conductor interface 220 or the transmission line bundle 112. Thus, in addition to the intraluminal imaging device 102 being navigable through tortuous bends without kinking, the scanner assembly 110 may remain functional during such navigation. In other words, the intraluminal imaging device 102 may remain functional as the intraluminal imaging device is navigated through a bend at least at the illustrated radius of curvature 300.

Figure 6:
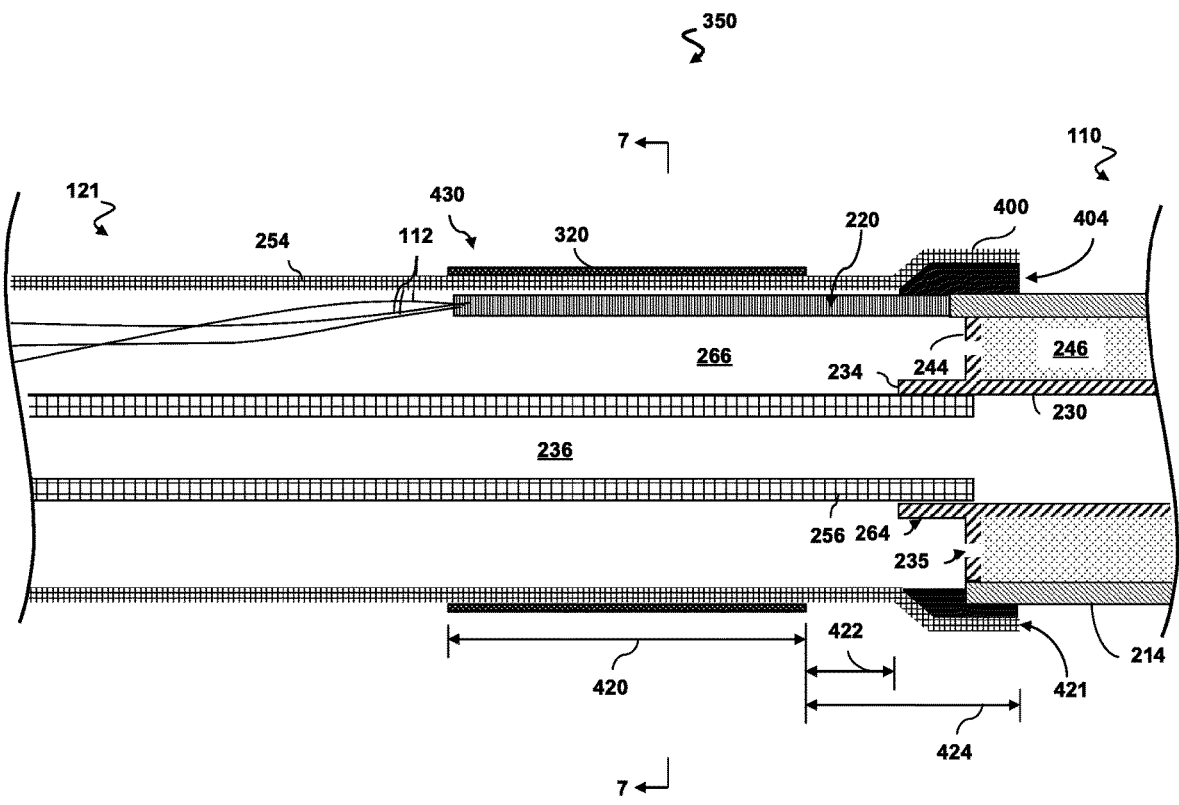
FIG. 6 is a diagrammatic, cross-sectional side view of a distal portion of an intraluminal imaging device, in accordance with at least one embodiment of the present disclosure.

FIG. 6 is a diagrammatic cross-sectional side view of a distal portion 350 of an example intraluminal imaging device (e.g., intraluminal imaging device 102), according to aspects of the present disclosure. In particular, FIG. 6 illustrates a distal portion of the outer member 254 (e.g., an outer shaft), which is reinforced by a reinforcement layer 320 and includes a flared opening 400. In some embodiments, the flared opening 400 may be sized to receive the scanner assembly 110. For instance, a proximal end of the scanner assembly 110 may be wider than an unflared portion of the outer member 254, and, in such cases, the flared opening 400 may be shaped to increase a diameter of outer member 254 from a first diameter to a second diameter to accommodate the diameter of the scanner assembly 110. Additionally or alternatively, the flared opening 400 may be shaped to receive the conductor interface 220. Although the conductor interface 220 is illustrated as having a regular shape (e.g., one or more planar profiles), the conductor interface 220 may alternatively be implemented with an irregular shape and/or bend along a curved path. Examples of conductor interfaces are disclosed in U.S. Patent Application No. 63/056,172, titled "CURVED CIRCUIT SUBSTRATE FOR INTRALUMINAL ULTRASOUND IMAGING ASSEMBLY," and filed Jul. 24, 2020, which is hereby incorporated by reference in its entirety. Further, in some embodiments, an adhesive 404 may be used to couple the outer member 254 to the scanner assembly 110. For instance, the adhesive 404 may fill a space between the flared opening 400 and the scanner assembly 110, as illustrated. In other embodiments, the outer member 254 may maintain a relatively constant diameter, as illustrated in FIG. 4.

As described herein, the reinforcement layer 320 may be formed from a polymer. For instance, the reinforcement layer 320 may include a polyimide, polyamide, thermoplastic elastomer like PEBAX®, or PTFE. In particular, the reinforcement layer 320 may be formed from a material that may be coupled (e.g., combined) with the outer member 254 via thermal reflow (e.g., thermal bond and/or thermal fusing). Moreover, as described above, the reinforcement layer 320 may be selected to produce a region of the outer member 254 with a hardness less than the scanner assembly 110 and greater than a hardness of another region of the outer member lacking the reinforcement layer 320 so that the stiffness of the intraluminal imaging device 102 transitions proximally to distally from a relatively lower stiffness (e.g., corresponding to the outer member 254) to a relatively higher stiffness (e.g., corresponding to the imaging assembly 110). To that end, in some embodiments, a material with a hardness less than a hardness of the outer member 254 may be selected for the reinforcement layer 320. In some cases, a durometer of the reinforcement layer 320 may be less than or equal to 55 Shore D (e.g., Pebax® 55D), for example, and a durometer of the outer member 254 may be greater than or equal to 55 Shore D (e.g., Pebax® 70D). Further, in some cases, the outer member 254 and the reinforcement layer may include the same material, such as the same type of thermoplastic elastomer, with different respective hardness. For example, the outer member 254 may be formed from Pebax® with a first durometer, and the reinforcement layer 320 may be formed from Pebax® with a second durometer.

As illustrated in FIG. 6, the reinforcement layer 320 may extend over a region of the outer member 254. In particular, the reinforcement layer 320 may extend over a length 420, which may correspond to the length of the region. As an illustrative example, the length 420 may be between 5 millimeters (mm) and 15 mm, including values such as 5 mm, 7 mm, mm, 10 mm, 12 mm, and 15 mm, or other values both larger and smaller. In some embodiments, the reinforcement layer 320 and/or the region of the outer member 254 coupled with the reinforcement layer 320 may be spaced from a distal end 421 of the outer member 254. For instance, length 422 may represent the distance between the reinforcement layer 320 and the flared opening 400, and length 424 may represent the distance between the reinforcement layer 320 and the distal end 421 of the outer member 254. In some embodiments, length 422 and/or length 424 may be greater than or equal to 1 mm. In particular, length 422 and/or length 424 may be between approximately 1.0 mm and 1.5 mm. To that end, the reinforcement layer 320 may be spaced between 1.0 mm and 1.5 mm from the flared opening 400 of the proximal outer member, and/or the reinforcement layer 320 may be spaced between 1.0 mm and 1.5 mm from the distal end 421. In some embodiments, spacing the reinforcement layer 320 from the flared opening 400 (e.g., by the length 422) may minimize the diameter of the intraluminal imaging device 102 at the site of the coupling between the outer member 254 and the scanner assembly 110 (e.g., at the flared opening 400). Further, in some embodiments, a thickness of the reinforcement layer 320 may be greater than or equal to 0.001". For instance, the thickness may be between 0.001"-0.005". In particular, the thickness of the reinforcement layer 320 may be selected so that the outer diameter of the region of the outer member reinforced by the reinforcement layer 320 does not exceed the outer diameter of the scanner assembly 110. Cut plane 7-7 shows a cross-sectional plane through the distal portion of the intraluminal imaging device 102, which is shown in greater detail in FIG. 7.

As illustrated, the position and extent of the reinforcement layer 320 may be defined at least in part by the length 420, the length 422, and/or the length 424. Moreover, the reinforcement layer 320 may be further defined by a thickness and a material, which may have a certain hardness. In some embodiments, a combination of one or more parameters, such as the length 420, the length 422 and/or the length 424, the thickness, and/or the material, may be selected for the reinforcement layer 320 so that the intraluminal imaging device 102 exhibits certain properties. In particular, the one or more parameters may be selected so that the intraluminal imaging device 102 may bend (e.g., at the outer member 254) to a particular radius of curvature without kinking. For instance, the one or more parameters may be selected so that the intraluminal imaging device may bend to a smaller radius of curvature without kinking in comparison with an intraluminal imaging device lacking the reinforcement layer 320. Moreover, the one or more parameters may be selected so that the outer member 254 may support the mass of the scanner assembly 110 and/or the mass of the intraluminal imaging device 100 distal of the outer member 254. For instance, the one or more parameters may be selected to provide a column strength that enables the intraluminal imaging device 100 to be navigable (e.g., pushable) through tortuous vasculature.

In the illustrated embodiment, the extent and positioning of the reinforcement layer 320 affected by the length 420 and one or both of the length 422 and/or the length 424 produce a proximal portion 430 of the reinforcement layer that extends over the conductor interface 220. More specifically, the illustrated reinforcement layer 320 extends over a portion of the conductor interface 220 where the one or more conductors of the transmission line bundle 112 may physically and/or electrically couple to the conductor interface 220. As such, the reinforcement layer 320 further extends over at least a portion of one or more conductors of the transmission line bundle 112. Because the conductor interface 220 may affect the stiffness (e.g., flexibility) of the intraluminal imaging device 102, the reinforcement layer 320 may transition the stiffness of the outer member 254 at a proximal end of the conductor interface 220. In particular, the reinforcement layer 320 may be positioned so that the connection between the transmission line bundle 112 and the connector interface 220 is not disturbed (e.g., pinched off) by bending of the outer member 254 during navigation of the intraluminal imaging device 102 within a patient's vasculature.

Figure 7:
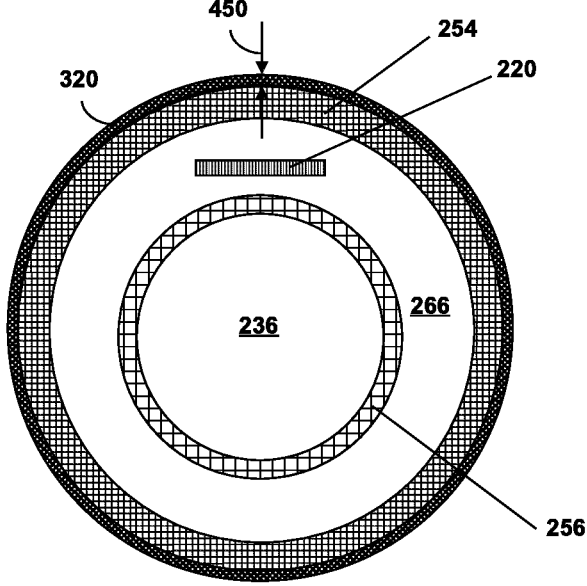
FIG. 7 is a diagrammatic, cross-sectional view of cut plane 7-7 from FIG. 6, in accordance with at least one embodiment of the present disclosure.

FIG. 7 is a diagrammatic, cross-sectional perspective view of cut plane 7-7 from FIG. 6. As shown, the inner member 256, the interior of which defines lumen 236, is visible. The cross-sectional perspective view of cut plane 7-7 further includes the outer member 254, the interior of which defines the space 266. The conductor interface 220 is positioned within the space 266, and the reinforcement layer 320, which includes a thickness 450, is coupled directly with the outer member 254. As described herein, the thickness 450 may be greater than or equal to approximately 0.001". Moreover, while the reinforcement layer 320 is illustrated as a single layer, it may be appreciated that the reinforcement layer 320 may include a stack of layers with a combined total thickness 450.

Figures 8A, 8B:
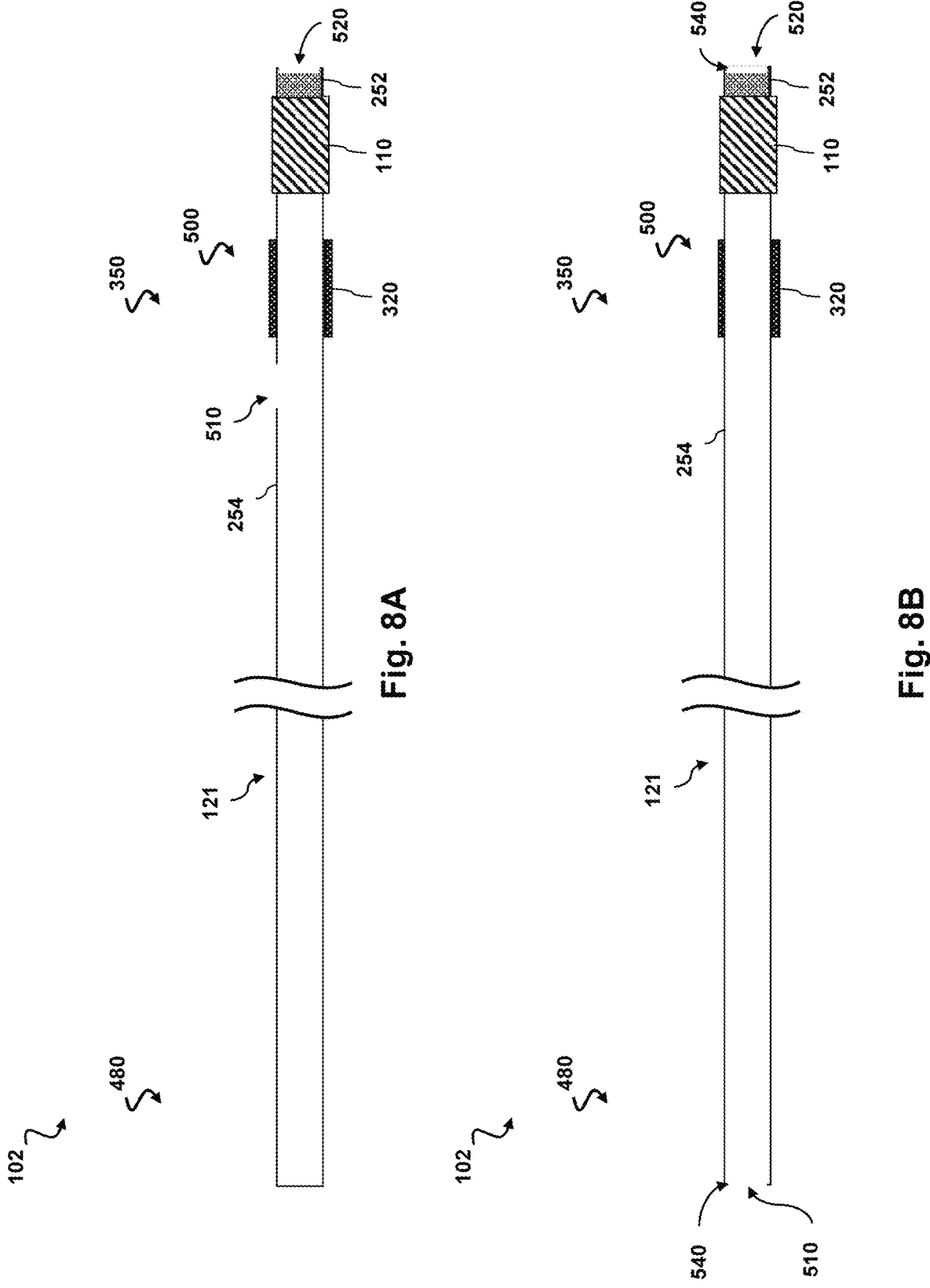
FIG. 8A is a diagrammatic schematic view of an intraluminal imaging device, in accordance with at least one embodiment of the present disclosure.
FIG. 8B is a diagrammatic schematic view of an intraluminal imaging device, in accordance with at least one embodiment of the present disclosure.

As illustrated in FIGS. 8A-B, the reinforcement layer 320 may be coupled with the flexible elongate member 121 of the intraluminal imaging device 102 at a distal portion 500 of the flexible elongate member, which may include the outer member 254 (e.g., an outer shaft of the flexible elongate member), as described herein. FIG. 8A is a diagrammatic schematic view of an example intraluminal imaging device 102, which includes a flexible elongate member 121 having a proximal portion 480 and the distal portion 500. As further illustrated in FIG. 8A, in some embodiments, the flexible elongate member 121 may be a rapid-exchange catheter. To that end, the flexible elongate member 121 may include a guidewire entry port 510 and a guidewire exit port 520 positioned in the distal portion 500 of the flexible elongate member. In some cases, the guidewire exit port 520 may be at a distal end of the distal member 252. Moreover, the reinforcement layer 320 may be coupled with the flexible elongate member 121 distal of the guidewire entry port 510. That is, for example, the reinforcement layer 320 may be positioned between the guidewire entry port 510 and the scanner assembly 110 within the distal portion 500 of the flexible elongate member.

FIG. 8B is a diagrammatic schematic view of an example intraluminal imaging device 102, where the flexible elongate member 121 is implemented as an over-the-wire catheter. More specifically, in the illustrated example, the guidewire entry port 510 is positioned at a proximal end 540 of the flexible elongate member (e.g., within the proximal portion 480). In this way, the flexible elongate member 121 may be implemented so that the flexible elongate member 121 can extend over a guide wire (e.g., guide wire 118) from a proximal end 540 to a distal end 550 of the flexible elongate member. As further illustrated by FIG. 8B, in embodiments where the flexible elongate member 121 is an over-the-wire catheter, the reinforcement layer 320 may be positioned in the distal portion 500 of the flexible elongate member. In particular, the reinforcement layer 320 may be spaced from and proximate to the scanner assembly 110.

Figure 9:
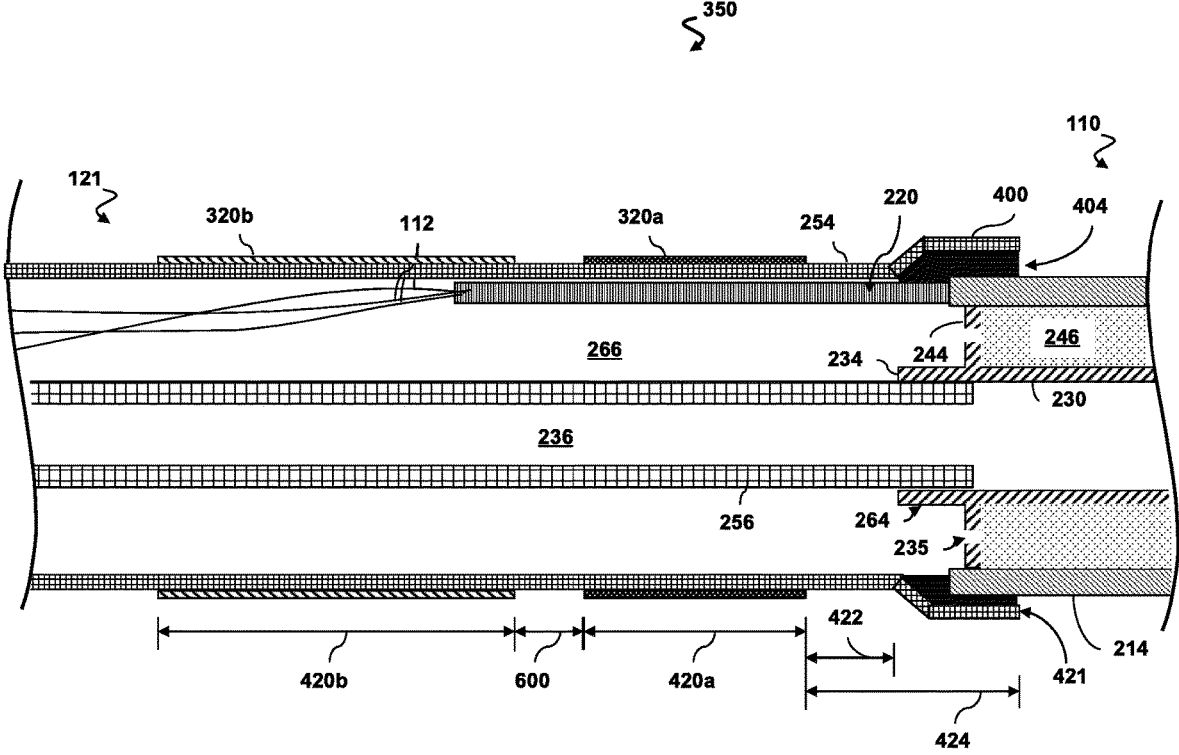
FIG. 9 is a diagrammatic, cross-sectional side view of a distal portion of an intraluminal imaging device, in accordance with at least one embodiment of the present disclosure.

In some embodiments, the intraluminal imaging device 102 may include multiple reinforcement layers, as illustrated in FIG. 9. FIG. 9 is a diagrammatic cross-sectional side view of a distal portion 350 of an example intraluminal imaging device (e.g., intraluminal imaging device 102), according to aspects of the present disclosure. In particular, FIG. 9 illustrates a first reinforcement layer 320a extending over and coupled to a first region of the outer member 254 and a second reinforcement layer 320b extending over and coupled to a second region of the outer member 254. As illustrated, the first reinforcement layer 320a and the second reinforcement layer 320b may be positioned proximate the scanner assembly 110 when the outer member 254 is joined with the scanner assembly 110 (e.g., positioned at a distal region of the flexible elongate member 121). As described below, one or more parameters associated with the reinforcement layers 320a-b may be selected, which may impact a characteristic, such as stiffness, of the outer member 254. Because parameters and the relationship of respective parameters between the first and the second reinforcement layer (e.g., 320a and 320b, respectively) may be tuned, the impact on this characteristic may be more finely adjusted in some cases. For instance, the flexibility of the outer member 254 may be more finely adjusted by the reinforcement layers 320a-b in comparison with a single reinforcement layer. Further, for the purposes of example, embodiments are illustrated and described as having one or two reinforcement layers. However, it may be appreciated that any suitable number of reinforcement layers may be included in the intraluminal imaging device 102.

In some embodiments, the reinforcement layers 320a-b may transition a stiffness of the outer member 254 proximate the scanner assembly 110. Moreover, the reinforcement layers 320a-b may transition the stiffness uniformly or non-uniformly with respect to one another. That is, for example, the reinforcement layers 320a-b may include similar features or may vary from one another. For instance, the first reinforcement layer 320a and the second reinforcement layer 320b may be equal in length, or, as illustrated, the first reinforcement layer 320a and the second reinforcement layer 320b may have different lengths (e.g., may extend over regions of varying lengths). The illustrated length 420a of the first reinforcement layer 320a is less than the length 420b of the second reinforcement layer 320b, for example. It may be appreciated that the length 420a may be greater than the length 420b in other embodiments. Further, while the reinforcement layers 320a-b may be composed of the same or different materials. In some embodiments, for example, the reinforcement layers 320a-b may include the same type of polymer (e.g., thermoplastic elastomer) or may include different types of polymers. In addition, a hardness of the reinforcement layers 320a-b may be the same or different. In some cases, the hardness of each of the reinforcement layers 320a-b may be less than a hardness of the outer member 254. Moreover, a thickness of the reinforcement layers 320a-b may be the same or different.

As further illustrated, the reinforcement layers 320a-b may be spaced from one another. For instance, the reinforcement layers 320a-b may be separated by a distance 600. Alternatively, in some embodiments, the reinforcement layers 320a-b may be immediately adjacent to one another. Further, in some embodiments, one or both of the reinforcement layers 320a-b may be positioned so that the layers extend over a proximal end of the conductor interface 220.

In the illustrated embodiment, for example, the second reinforcement layer 320*b* extends over the proximal end of the conductor interface 220. Moreover, as described with reference to FIG. 6, the length 422 between a distal end of the first reinforcement layer 320*a* and the flared opening 400 and/or the length 424 between the distal end of the first reinforcement layer 320*a* and the distal end 421 of the outer member 254 may be selected to affect certain characteristics (e.g., stiffness) of the outer member 254.

Figure 10:
FIG. 10 is a flow chart of a method for assembling an intraluminal imaging device, in accordance with at least one embodiment of the present disclosure.
Figure 10:
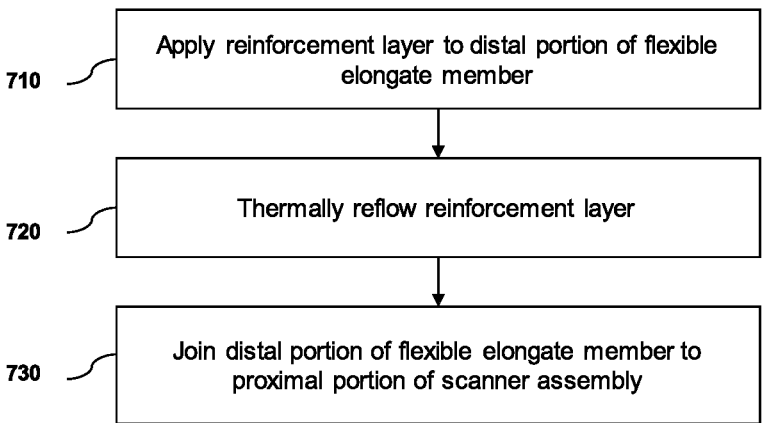

FIG. 10 is a flow diagram of a method 700 of assembling an intraluminal imaging device, according to aspects of the present disclosure. As illustrated, the method 700 includes a number of enumerated steps, but embodiments of the method 700 may include additional steps before, after, or in between the enumerated steps. In some embodiments, one or more of the enumerated steps may be omitted, performed in a different order, or performed concurrently.

At step 710, the method 700 may include applying a reinforcement layer to a distal portion of a flexible elongate member. For instance, a reinforcement layer, such as rein-forcement layer 320 (FIG. 5) may be applied to an outer member (e.g., outer member 254) positioned at the distal portion of the flexible elongate member (e.g., flexible elon-gate member 121). In some embodiments, applying the reinforcement layer to the distal portion of the flexible elongate member may involve wrapping a layer of material around the flexible elongate member and/or positioning a sleeve around the distal portion of the flexible elongate member. Additionally or alternatively, applying the rein-forcement layer may involve depositing the layer, coating the layer, and/or the like upon the distal portion of the flexible elongate member.

In some embodiments, before the reinforcement layer is applied to the flexible elongate member, the flexible elon-gate member and/or the reinforcement layer may be pre-pared. For instance, the flexible elongate member and/or the reinforcement layer may be cleaned (e.g., with an alcohol wipe) or otherwise prepared for coupling. Further, the rein-forcement layer applied to the flexible elongate member may be selected to alter one or more characteristics of the flexible elongate member. For instance, a region of the flexible elongate member coupled with the reinforcement layer may bend to a radius of curvature without kinking that is different than the radius of curvature that the region could bend to without kinking when the region is not coupled to the reinforcement layer. In particular, the reinforcement layer may be selected and/or positioned so that, when coupled to the reinforcement layer, the region may bend to a smaller radius of curvature (e.g., make a tighter turn) without kinking than the region could otherwise bend to without kinking. To that end, applying the reinforcement layer to the flexible elongate member may involve positioning the rein-forcement layer so that the reinforcement layer is spaced from a distal end of the flexible elongate member (e.g., spaced from a distal end of an outer member of at the distal portion of the flexible elongate member), as described herein. Moreover, applying the reinforcement layer may involve applying a reinforcement layer with a particular length, thickness, hardness, and/or the like. As an illustrative example, the reinforcement layer may have a length of 7 mm, a thickness greater than or equal to 0.001", a durometer less than or equal to 55 Shore D, or a combination thereof. Additionally or alternatively, the characteristics, including the positioning, of the reinforcement layer may be selected so that the reinforcement layer extends over a proximal end of a conductor interface (e.g., conductor interface 220) when the flexible elongate member is joined with (e.g., coupled to)

an imaging assembly (e.g., scanner assembly 110). Further, the characteristics of the reinforcement layer may be selected so that the hardness of the reinforcement layer is less than the hardness of the region of the flexible elongate member that the reinforcement layer is applied to.

At step 720, the method 700 may involve thermally reflowing (e.g., bonding and/or fusing) the reinforcement layer with the flexible elongate member (e.g., with the outer member of the flexible elongate member). More specifically, the method 700 may involve coupling the reinforcement layer with a region of the flexible elongate member (e.g., a region within the distal portion of the flexible elongate member) via a thermal reflow (e.g., thermal bonding). To that end, the material of the reinforcement layer and the material of the region of the flexible elongate member may be warmed (e.g., melted) such that the reinforcement layer and the region of the flexible elongate member are fused together. In some embodiments, for example, thermally reflowing the reinforcement layer may involve the use of a thermal split die bonder, which may heat the reinforcement layer and/or the region. As an illustrative example, the reinforcement layer and/or the region may be heated with a temperature of 375° F. for 15 seconds to affect the thermal reflow.

At step 730, the method 700 may involve joining the distal portion of the flexible elongate member to a proximal portion of a scanner assembly (e.g., scanner assembly 110). More specifically, the method 700 may involve joining the distal portion of the flexible elongate member, which includes a region that the reinforcement layer is coupled to and extends over, to the proximal portion of the scanner assembly. Joining the distal portion of the flexible elongate member with the proximal portion of the scanner assembly may involve sliding a flared opening at a distal end of the flexible elongate member over the proximal portion of the scanner assembly. The joining may further involve applying an adhesive so that the flexible elongate member and the scanner assembly are fixedly coupled. For instance, an adhesive may be applied between the flexible elongate member and the scanner assembly within the flared opening. Any other suitable method of joining the flexible elongate member and the scanner assembly, such as thermally cou-pling, a pressure fit, interference fit, clamping, and/or the like may additionally or alternatively be employed.

While joining the distal portion of the flexible elongate member and the proximal portion of the scanner assembly is illustrated and described herein as occurring after the rein-forcement layer is applied and coupled via a thermal reflow to (e.g., fused with) the flexible elongate member, embodi-ments are not limited thereto. In some embodiments, for example, the reinforcement layer may be applied and/or coupled to the flexible elongate member via a thermal reflow after the flexible elongate member is joined with the scanner assembly. Further, it may be appreciated that before the flexible elongate member is joined with the scanner assem-bly, a flexible substrate (e.g., flexible substrate 214) of the scanner assembly may be wrapped around a support member (e.g., support member 230).

A person of ordinary skill in the art will recognize that the present disclosure advantageously provides an intraluminal imaging system that enables both pushability and flexibility for navigating an imaging assembly through human vascu-lature. In particular, the intraluminal imaging system enables navigation of the imaging assembly through tortuous vas-culature by preventing kinking of a portion of the imaging assembly along a tight bend. The logical operations making up the embodiments of the technology described herein are referred to variously as operations, steps, objects, elements, components, regions, etc. Furthermore, it should be understood that these may occur in any order, unless explicitly claimed otherwise or a specific order is inherently necessitated by the claim language.

It should further be understood that the described technology may be employed in a variety of different applications, including but not limited to human medicine, veterinary medicine, education and inspection. All directional references e.g., upper, lower, inner, outer, upward, downward, left, right, lateral, front, back, top, bottom, above, below, vertical, horizontal, clockwise, counterclockwise, proximal, and distal are only used for identification purposes to aid the reader's understanding of the claimed subject matter, and do not create limitations, particularly as to the position, orientation, or use of the intraluminal imaging system. Connection references, e.g., attached, coupled, connected, and joined are to be construed broadly and may include intermediate members between a collection of elements and relative movement between elements unless otherwise indicated. As such, connection references do not necessarily imply that two elements are directly connected and in fixed relation to each other. The term "or" shall be interpreted to mean "and/or" rather than "exclusive or." The word "comprising" does not exclude other elements or steps, and the indefinite article "a" or "an" does not exclude a plurality. Unless otherwise noted in the claims, stated values shall be interpreted as illustrative only and shall not be taken to be limiting.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An intraluminal imaging device, comprising:
a flexible elongate member configured to be positioned within a body lumen of a patient, the flexible elongate member comprising a proximal portion and a distal portion;
an ultrasound scanner assembly configured to obtain ultrasound imaging data while positioned within the body lumen, wherein the ultrasound scanner assembly is coupled to and positioned distally of the distal portion of the flexible elongate member, wherein the distal portion of the flexible elongate member comprises a first polymer with a first hardness; and
a reinforcement layer extending over and directly contacting only a region of the distal portion of the flexible elongate member, wherein the region is spaced proximally from a proximal end of the ultrasound scanner assembly, wherein the reinforcement layer comprises a second polymer with a different, second hardness.

2. The device of claim 1, wherein the region and the reinforcement layer are coupled via thermal reflow.

3. The device of claim 1, wherein the region is spaced proximally from a distal end of the distal portion of the flexible elongate member.

4. The device of claim 3, wherein the region is spaced at least 1 millimeter from the distal end of the distal portion of the flexible elongate member.

5. The device of claim 1, wherein the second hardness is less than the first hardness.

6. The device of claim 1, wherein the reinforcement layer comprises a thermoplastic elastomer.

7. The device of claim 1, wherein the reinforcement layer comprises a thickness greater than or equal to 0.001 inches.

8. The device of claim 1, wherein the ultrasound scanner assembly comprises a conductor interface, wherein a proximal portion of the reinforcement layer extends over the conductor interface.

9. The device of claim 8, further comprising a plurality of conductors coupled to a proximal portion of the conductor interface, wherein the reinforcement layer extends over the plurality of conductors.

10. The device of claim 1, wherein a distal end of the flexible elongate member comprises a flared opening.

11. The device of claim 10, wherein the region is spaced proximally from the flared opening.

12. The device of claim 1, wherein the intraluminal imaging device is a rapid-exchange catheter comprising a guidewire entry port, wherein the guidewire entry port is disposed within the distal portion of the flexible elongate member, wherein the region is positioned distal of the guidewire entry port.

13. The device of claim 1, further comprising an additional reinforcement layer extending over and directly contacting only an additional region of the distal portion of the flexible elongate member, wherein the additional reinforcement layer comprises a third hardness different than the first hardness.

14. The device of claim 1, wherein the flexible elongate member is configured to bend to a radius of curvature within tortuous vasculature, and wherein the reinforcement layer is configured to decrease the radius of curvature to which the region of the flexible elongate member is bendable within the tortuous vasculature without kinking.

15. An intravascular ultrasound (IVUS) imaging catheter, comprising:
a catheter body configured to be positioned within a blood vessel of a patient, the catheter body comprising a proximal portion and a distal portion;
an ultrasound scanner assembly comprising a circumferential array of acoustic elements configured to obtain ultrasound imaging data while positioned within the blood vessel, wherein the ultrasound scanner assembly is coupled to and positioned distally of the distal portion of the catheter body, wherein the distal portion of the catheter body comprises a first polymer with a first hardness; and
a reinforcement layer extending over and directly contacting only a region of the distal portion of the catheter body, wherein the region is spaced proximally from a proximal end of the ultrasound scanner assembly, wherein the reinforcement layer comprises a second polymer with a different, second hardness less than the first hardness such that the region is bendable within a tortuous portion of the blood vessel without kinking.

* * * * *